US00PP11474P

United States Patent [19]

Boeder

[11] Patent Number: Plant 11,474

[45] Date of Patent: Aug. 8, 2000

[54] CHRYSANTHEMUM PLANT NAMED 'TOFFEE TIME'

[75] Inventor: Mark Boeder, West Wittering, United Kingdom

[73] Assignee: Cleangro Limited, West Sussex, United Kingdom

[21] Appl. No.: 09/082,265

[22] Filed: May 2, 1998

[51] Int. Cl.[7] ..... A01H 5/00

[52] U.S. Cl. ..... Plt./296

[58] Field of Search ..... Plt./296

*Primary Examiner*—Howard J. Locker

*Attorney, Agent, or Firm*—Christie, Parker & Hale, LLP

[57] ABSTRACT

A new variety of pot chrysanthemum producing large, bronze, anemone-type flowers suitable for pot forcing.

1 Drawing Sheet

BACKGROUND OF THE INVENTION

The present invention is directed to a new and distinct variety of chrysanthemum botanically classified as *Dendranthema grandiflora*. The varietal denomination of the new chrysanthemum is 'Toffee Time'.

The female parent of the new variety is an undistributed, unnamed variety identified as P402-90 and the male parent is an undistributed, unnamed variety identified as P64-89. The new variety has been asexually reproduced by vegetative cuttings in Ventura County, Calif. and the distinguishing characteristics are retained through successive generations of asexual reproduction.

SUMMARY OF THE INVENTION

'Toffee Time' is pot type chrysanthemum plant variety that produces large bronze, anemone-type flowers on a vigorous plant suitable for pot forcing.

BRIEF DESCRIPTION OF ILLUSTRATION

The accompanying photograph shows a typical specimen of the new variety with colors being as nearly true as possible with illustrations of this type.

DESCRIPTION OF THE PLANT

The following description of the new variety is of specimens grown in a greenhouse in Ventura County, Calif. in the month of November. 'Toffee Time' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once with center bud removed; however, 'Toffee Time' can be produced as a spray pot or center disbud plant. The illustration is of a spray potted plant. It has been observed that the shelf life of 'Toffee Time' is about 26 days with the response time of about 9 weeks. It may be also useful to provide one treatment of growth regulator B-9 at 2000 ppm. Useful growing conditions include night temperatures of about 64°–66° F., day temperatures of about 75°–85° F. and about 5,000–6,000 foot-candles of light.

Plant:

*Habit.*—Upright.

*Height.*—About 30 cm.

*Number of breaks from pinch.*—About 3.

*Typical container sizes commercially grown in.*—6 inch and 8 inch pots.

*Length of lateral branches.*—About 20 cm.

*Stem color.*—Near 138B.

Foliage:

*Leaf arrangement.*—Alternate.

*Number of leaves per lateral branch.*—About 10.

*Leaf size.*—Length: About 7.7 cm. Width: About 4.3 cm.

*Leaf shape.*—Ovate.

*Attachment.*—Petioled.

*Leaf apex.*—Acute.

*Base.*—Tapered.

*Margin.*—Serrate.

*Aspect.*—Flat.

*Surface.*—Top: Pubescent. Bottom: Highly pubescent.

*Venation.*—Net, prominent mid vein on underside; underside near 137B, upper side near 146D.

*Petiole length.*—About 1.8 cm. Color: Near 138B.

*Stipule characteristics.*—Infrequently present; when present about 3 acute lobes.

*Color.*—Mature leaf: Top: Near 137A. Bottom: Near 137B. Young leaf: Top: Near 137B. Bottom: Near 137C.

Flower:

*Inflorescence form.*—Cyme.

*Flower form.*—Anemone.

*Number of blooms per branch.*—About 5.

*Depth of fully expanded bloom.*—About 3 cm.

*Sepal numbers.*—About 25. Color: Near 137C.

*General appearance of sepals.*—Highly membranous.

*Peduncle.*—Length: Lowermost, longest peduncle is about 9.5, terminal peduncle is about 4.2 cm. Habit: Straight, upright. Surface: Highly pubescent. Strength: Very sturdy.

*Flower bud shape.*—Slightly irregular, flattened sphere. Diameter: About 1.2 cm. Height: About 0.7 cm. Size: Diameter of fully expanded bloom is about 10.5 cm, diameter of anemone center is about 2.5 cm.

*Ray florets.*—Number per flower: About 35. Shape: Elliptic. Apex: 3 lobed. Base: Tapered. Margin: Entire. Aspect: Slightly reflexed. Length: About 5.5 cm. Width: About 1.4 cm.

*Disc florets.*—Number per flower: About 230. Shape: Cylindrical, splitting with age. Length: About 1.4 cm. Width: About 0.2 cm.

*Fragrance.*—Strong, musky.

Flower color:

*General flower coloration.*—Reddish/gold anemone, with slightly lighter disc color, disc coloration is slightly lighter than the rest of the flower.

*Ray florets, top side*.—Immature: Near 26A. Mature: Near 31A. Fading: Near 31B.

*Ray floret, under side*.—Immature: Near 26B. Mature: Near 318. Fading: Near 26B.

*Disc florets*.—Immature: Near 144B. Mature: Near 7A. Fading: Near 26B.

*Changes as the flower ages*.—Center of flower loses green eye, disc flowers become loosely held, initially ray florets deepen in color as flower matures with red tones more apparent, overall ray floret color becomes slightly lighter while maintaining same color tones.

Reproductive organs:

*Ray florets*.—Pistillate. Stigma shape: 2 forked. Stigma color: Near 6A. Style length: About 0.5 cm.

*Disc florets*.—Stigma shape: 2 forked. Stigma color: Near 12B. Style length: About 0.4 cm. Stamen number: About 5. Anther length: About 0.3 cm. Pollen color: Near 17B. Pollen quantity: Abundant.

What is claimed is:

1. A new and distinct chrysanthemum plant of the variety substantially as herein shown and described.

* * * * *

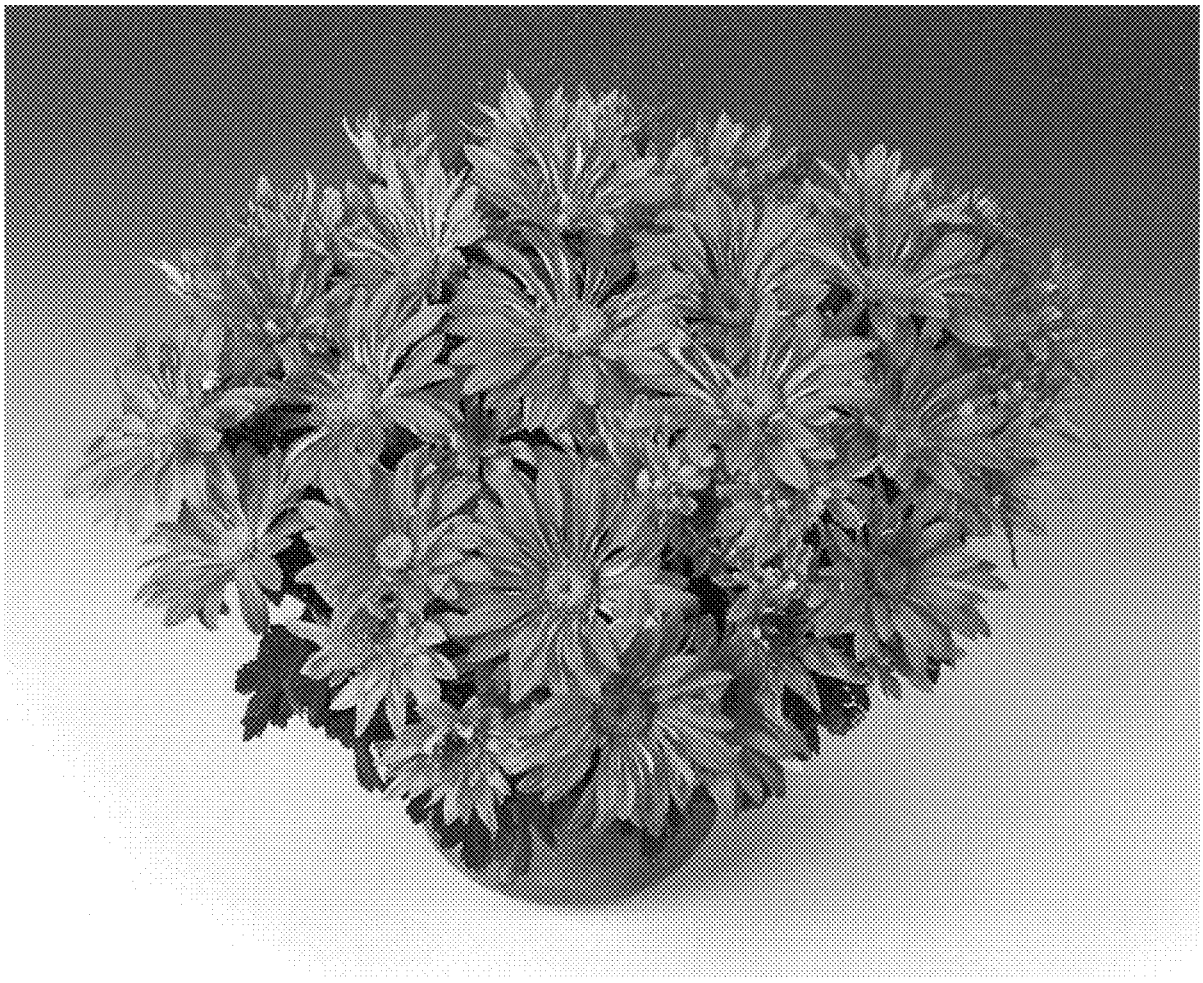

UNITED STATES PATENT AND TRADEMARK OFFICE

CERTIFICATE OF CORRECTION

PATENT NO. : PP 11,474
DATED : August 8, 2000
INVENTOR(S) : Mark Boeder

It is certified that error appears in the above-identified patent and that said Letters Patent is hereby corrected as shown below:

Title page,
Filed Date, change from "May 2, 1998" to -- May 20, 1998 --

Signed and Sealed this

Fifth Day of March, 2002

*Attest:*

*Attesting Officer*

JAMES E. ROGAN
*Director of the United States Patent and Trademark Office*